(12) United States Patent
Moscoso et al.

(10) Patent No.: US 6,613,302 B1
(45) Date of Patent: Sep. 2, 2003

(54) UZM-5, UZM-5P AND UZM-6: CRYSTALLINE ALUMINOSILICATE ZEOLITES AND PROCESSES USING THE SAME

(75) Inventors: Jaime G. Moscoso, Mt. Prospect, IL (US); Gregory J. Lewis, Mt. Prospect, IL (US); Mark A. Miller, Niles, IL (US); Deng-Yang Jan, Elk Grove Village, IL (US); R. Lyle Patton, Rolling Meadows, IL (US); Lisa M. Rohde, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 319 days.

(21) Appl. No.: 09/705,860

(22) Filed: Nov. 3, 2000

(51) Int. Cl.$^7$ ............................................... C01B 39/48
(52) U.S. Cl. ........................... 423/718; 423/705; 208/46
(58) Field of Search ................. 423/705, 718; 208/46

(56) References Cited

U.S. PATENT DOCUMENTS

| | | | | |
|---|---|---|---|---|
| 3,306,922 A | * | 2/1967 | Barrer et al. ................ 556/173 |
| 3,832,449 A | * | 8/1974 | Rosinski et al. ............. 423/705 |
| 3,972,983 A | * | 8/1976 | Ciric ........................... 423/705 |
| 4,060,590 A | * | 11/1977 | Whittam et al. ............. 423/718 |
| 4,287,166 A | * | 9/1981 | Dwyer et al. ................ 423/705 |
| 4,533,649 A | * | 8/1985 | Ball et al. ...................... 502/71 |
| 4,857,288 A | * | 8/1989 | Marcus et al. .............. 423/703 |
| 4,879,103 A | * | 11/1989 | Vaughan ..................... 423/705 |
| 4,954,325 A | * | 9/1990 | Rubin et al. ................. 423/706 |
| 5,108,579 A | * | 4/1992 | Casci ........................... 208/46 |
| 5,202,014 A | | 4/1993 | Zones et al. |

* cited by examiner

*Primary Examiner*—David Sample
(74) *Attorney, Agent, or Firm*—John G. Tolomei; Frank S. Molinaro

(57) ABSTRACT

A new family of crystalline alumino-silicate zeolites has been synthesized. These zeolites are represented by the empirical formula.

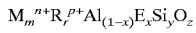

$$M_m^{n+}R_r^{p+}Al_{(1-x)}E_xSi_yO_z$$

where M is an alkali or alkaline earth metal such as lithium and strontium, R is a nitrogen containing organic cation such as tetramethyl ammonium and E is a framework element such as gallium. They are also characterized by unique x-ray diffraction patterns and have catalytic properties for carrying out various hydrocarbon conversion processes.

28 Claims, No Drawings

UZM-5, UZM-5P AND UZM-6: CRYSTALLINE ALUMINOSILICATE ZEOLITES AND PROCESSES USING THE SAME

FIELD OF THE INVENTION

This invention relates to a family of related crystalline aluminosilicate zeolites examples of which have been designated UZM-5, UZM-5P and UZM-6. These compositions are structurally different from other zeolites and can catalyze various hydrocarbon processes.

BACKGROUND OF THE INVENTION

Zeolites are crystalline aluminosilicate compositions which are microporous and which have a three-dimensional oxide framework formed from corner sharing $AlO_2$ and $SiO_2$ tetrahedra. Numerous zeolites, both naturally occurring and synthetically prepared are used in various industrial processes. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure.

The number of synthetic zeolites is well over a hundred as evidenced by the Atlas of Zeolite Structure Types published by the International Zeolite Association (IZA). As is well known, zeolites are distinguished from each other on the basis of their composition, crystal structure and adsorption properties. One method commonly used in the art to distinguish zeolites is x-ray diffraction.

Applicants have synthesized a family of crystalline zeolitic compositions which have unique x-ray diffraction patterns and have an empirical formula on an anhydrous basis in terms of molar ratios of:

$$M_m^{n+}R_r^{p+}Al_{(1-x)}E_xSi_yO_z$$

where M is at least one exchangeable cation selected from the group consisting of alkali and alkaline earth metals, "m" is the mole ratio of M to (Al+E) and varies from about 0 to about 1.2, R is a nitrogen-containing organic cation selected from the group consisting of quaternary ammonium ions, protonated amines, protonated diamines, protonated alkanolamines, quaternary alkanolammonium ions, diquaternary ammonium ions, and mixtures thereof, "r" is the mole ratio of R to (Al+E) and has a value of about 0.25 to about 3.0, E is an element selected from the group consisting of Ga, Fe, In, Cr, and B, "x" is the mole fraction of E and varies from 0 to about 0.5, "n" is the weighted average valence of M and has a value of +1 to about +2, "p" is the weighted average valence of R and has a value of +1 to about +2, "y" is the mole ratio of Si to (Al+E) and varies from about 5 to about 12, and "z" is the mole ratio of O to (Al+E) and has a value determined by the equation:

$$z=(m \cdot n+r \cdot p+3+4 \cdot y)/2$$

Specific members of this family of zeolites are: UZM-5, UZM-5P and UZM-6. These zeolites can catalyze various hydrocarbon conversion processes such as alkylation of benzene and isomerization of xylene.

SUMMARY OF THE INVENTION

This invention relates to a new family of zeolite, a process for preparing the zeolites and a process using the zeolites.

Accordingly, one embodiment of the invention is a microporous crystalline zeolite having a composition in the as synthesized form in terms of mole ratios of the elements given by $$M_m^{n+}R_r^{p+}Al_{(1-x)}E_xSi_yO_z$$

where M is at least one exchangeable cation selected from the group consisting of alkali and alkaline earth metals, "m" is the mole ratio of M to (Al+E) and varies from about 0 to about 1.2, R is a nitrogen-containing organic cation selected from the group consisting of protonated amines, protonated diamines, protonated alkanolamines, quaternary ammonium ions, diquaternaryammonium ions, quaternized alkanolamines and mixtures thereof, "r" is the mole ratio of R to (Al+E) and has a value of about 0.25 to about 3.0, E is an element selected from the group consisting of Ga, Fe, In, Cr, B, and mixtures thereof "x" is the mole fraction of E and varies from 0 to 0.5, "n" is the weighted average valence of M and has a value of about +1 to about +2, "p" is the weighted average valence of R and has a value of +1 to about +2, "y" is the mole ratio of Si to (Al+E) and varies from about 5 to about 12 and "z" is the mole ratio of O to (Al+E) and has a value determined by the equation:

$$z=(m \cdot n+r \cdot p+3+4 \cdot y)/2$$

the material characterized in that it has at least two x-ray diffraction peaks, one at a d-spacing of 3.9±0.12 Å and one at 8.6±0.20 Å.

In a particular embodiment, the zeolite is designated UZM-5 and has the diffraction pattern having at least the d-spacings and intensities set forth in Table A:

TABLE A

| | UZM-5 | |
|---|---|---|
| 2-θ | d(Å) | I/I$_o$ % |
| 6.31–5.89 | 14.00–15.00 | w–m |
| 7.96–7.58 | 11.10–11.65 | m–s |
| 10.40–10.01 | 8.50–8.83 | w–m |
| 12.11–11.59 | 7.30–7.63 | m |
| 16.10–15.53 | 5.50–5.70 | m–vs |
| 19.28–18.55 | 4.60–4.78 | w–m |
| 22.26–21.60 | 3.99–4.11 | m |
| 23.20–22.43 | 3.83–3.96 | w–s |
| 24.16–23.33 | 3.68–3.81 | vs |
| 30.48–29.55 | 2.93–3.02 | w–m |
| 31.94–30.92 | 2.80–2.89 | w–m |
| 44.83–43.47 | 2.02–2.08 | w |

Another embodiment of the invention is a process for preparing the above-described zeolites which comprises forming a reaction mixture containing reactive sources of R, Al, Si and optionally E and/or M and heating the reaction mixture at a temperature of about 100° C. to about 175° C., the reaction mixture having a composition expressed in terms of mole ratios of the oxides of:

$$aM_{2/n}O:bR_{2/p}O:(1-c)Al_2O_3:cE_2O_3:dSiO_2:eH_2O$$

where "a" has a value of about 0 to about 2.0, "b" has a value of about 1.5 to about 30, "c" has a value of about 0 to about 0.5, "d" has a value of 5 to about 30, and "e" has a value of about 30 to about 6000.

Yet another embodiment of the invention is a hydrocarbon conversion process using the above-described zeolites. More specifically the hydrocarbon conversion process is the alkylation of benzene with an olefin or the isomerization of xylenes.

These and other objects and embodiments will become more apparent after the following detailed description of the invention.

DETAILED DESCRIPTION OF THE INVENTION

Applicants have synthesized a new family of zeolites. In its as-synthesized form, this family of zeolites has a composition on an anhydrous basis that is represented by the formula:

$$M_m^{n+}R_r^{p+}Al_{(1-x)}E_xSi_yO_z$$

M is an exchangeable cation and is selected from the group consisting of alkali and alkaline earth metals. Specific examples of the M cations include but are not limited to lithium, sodium, potassium, cesium, strontium, calcium, magnesium, barium and mixtures thereof. The value of "m" which is the mole ratio of M to (Al+E) varies from 0 to about 1.2. R is a nitrogen containing organic cation and is selected from the group consisting of protonated amines, protonated diamines, protonated alkanolamines, quaternary ammonium ions, diquaternary ammonium ions, quaternized alkanolammonium ions and mixtures thereof. The value of "r" which is the mole ratio of R to (Al+E) varies from about 0.25 to about 3.0. The value of "n" which is the weighted average valence of M varies from +1 to about +2. The value of "p", which is the average weighted valence of the organic cation has a value from about +1 to about +2. E is an element which is present in the framework and is selected from the group consisting of gallium, iron, boron chromium, indium and mixtures thereof. The value of "x" which is the mole fraction of E varies from 0 to about 0.5. The ratio of silicon to (Al+E) is represented by "y" which varies from about 5 to about 12, while the mole ratio of O to (Al+E) is represented by "z" and " has a value given by the equation:

$$z=(m \cdot n+r \cdot p+3+4 \cdot y)/2$$

When M is only one metal, then the weighted average valence is the valence of that one metal, i.e. +1 or +2. However, when more than one M metal is present, the total amount of:

$$M_m^{n+} = M_{m1}^{(n1)+} + M_{m2}^{(n2)+} + M_{m3}^{(n3)+} + \ldots$$

and the weighted average valence "n" is given by the equation:

$$n = \frac{m_1 \cdot n_1 + m_2 \cdot n_2 + m_3 \cdot n_3 + \cdots}{m_1 + m_2 + m_3 \cdots}$$

Similarly when only one R organic cation is present, the weighted average valence is the valence of the single R cation, i.e., +1 or +2. When more than one R cation is present, the total amount of R is given by the equation:

$$R_r^{p+}=R_{r1}^{(p1)+}+R_{r2}^{(p2)+}+R_{r3}^{(p3)+}$$

and the weighted average valence "p" is given by the equation:

$$p = \frac{p_1 \cdot r_1 + p_2 \cdot r_2 + p_3 \cdot r_3 + \cdots}{r_1 + r_2 + r_3 + \cdots}.$$

These aluminosilicate zeolites, are prepared by a hydrothermal crystallization of a reaction mixture prepared by combining reactive sources of R, aluminum, optionally E and/or M and silicon in aqueous media. Accordingly, the aluminum sources include, but are not limited to, aluminum alkoxides, precipitated alumina, aluminum hydroxide, aluminum salts and aluminum metal. Specific examples of aluminum alkoxides include, but are not limited to aluminum orthosec-butoxide, and aluminum orthoisopropoxide. Sources of silica include but are not limited to tetraethylorthosilicate, fumed silicas, precipitated silicas and colloidal silica. Sources of the M metals include but are not limited to the halide salts, nitrate salts, acetate salts, and hydroxides of the respective alkali or alkaline earth metals. Sources of the E elements include but are not limited to alkali borates, boric acid, precipitated gallium oxyhydroxide, gallium sulfate, ferric sulfate, ferric chloride, chromium chloride, chromium nitrate, indium chloride and indium nitrate. When R is a quaternary ammonium cation, the sources include without limitation the hydroxide, and halide compounds. Specific examples include without limitation tetramethylammonium hydroxide, tetraethylammonium hydroxide, hexamethonium bromide, tetramethylammonium chloride, methyltriethylammonium hydroxide. R may also be neutral amines, diamines, and alkanolamines. Specific examples are triethanolamine, triethylamine, and N,N,N',N' tetramethyl-1,6-hexanediamine.

The reaction mixture containing reactive sources of the desired components can be described in terms of molar ratios of the oxides by the formula:

$$aM_{2/n}O:bR_{2/p}O:(1-c)Al_2O_3:cE_2O_3:dSiO_2:eH_2O$$

where "a" is the mole ratio of the oxide of M and has a value of 0 to about 2, "b" is the mole ratio of the oxide of R and has a value of about 1.5 to about 30, "d" is the mole ratio of silica and has a value of about 5 to about 30, "c" is the mole ratio of the oxide of E and has a value from 0 to about 0.5, and "e" is the mole ratio of water and has a value of about 30 to about 6000. The reaction mixture is now reacted at reaction conditions including a temperature of about 100° C. to about 175° C. and preferably from about 140° C. to about 160° C. for a period of about 12 hours to about 14 days and preferably for a time of about 2 days to about 5 days in a sealed reaction vessel under autogenous pressure. After crystallization is complete, the solid product is isolated from the heterogeneous mixture by means such as filtration or centrifugation, and then washed with de-ionized water and dried in air at ambient temperature up to about 100° C.

As synthesized, the zeolites will contain some of the exchangeable or charge balancing cations in its pores. These exchangeable cations can be exchanged for other cations, or in the case of organic cations, they can be removed by heating under controlled conditions. All of these methods are well known in the art.

The crystalline zeolites are characterized by a three-dimensional framework structure of at least $SiO_2$ and $AlO_2$ tetrahedral units. These zeolites are further characterized by their unique x-ray diffraction pattern. The x-ray diffraction pattern has at least two peaks: one peak at a d-spacing of about 3.9±0.12 Å and one peak at a d-spacing of about 8.6±0.20 Å. To allow for ready reference, the different structure types and compositions of crystalline zeolites have been given arbitrary designation of UZM-h, where "h" is an integer starting at one and where for example "1" represents a framework of structure type "1". That is one or more zeolitic composition with different empirical formulas can have the same structure type "h", e.g. "1".

In this respect, the following species can be identified by their x-ray diffraction patterns which have at least the d-spacing and relative intensities set forth in Tables A to C.

TABLE A

UZM-5

| 2-θ | d(Å) | I/I$_o$ % |
|---|---|---|
| 6.31–5.89 | 14.00–15.00 | w–m |
| 7.96–7.58 | 11.10–11.65 | m–s |
| 10.40–10.01 | 8.50–8.83 | w–m |
| 12.11–11.59 | 7.30–7.63 | m |
| 16.10–15.53 | 5.50–5.70 | m–vs |
| 19.28–18.55 | 4.60–4.78 | w–m |
| 22.26–21.60 | 3.99–4.11 | m |
| 23.20–22.43 | 3.83–3.96 | w–s |
| 24.16–23.33 | 3.68–3.81 | vs |
| 30.48–29.55 | 2.93–3.02 | w–m |
| 31.94–30.92 | 2.80–2.89 | w–m |
| 44.83–43.47 | 2.02–2.08 | w |

TABLE B

UZM-5P

| 2-θ | d(Å) | I/I$_o$ % |
|---|---|---|
| 6.31–5.19 | 14.00–17.00 | w–vs |
| 7.96–7.56 | 11.10–11.70 | w–m |
| 10.52–10.04 | 8.40–8.80 | m–s |
| 16.56–15.67 | 5.35–5.65 | w–m |
| 19.49–18.87 | 4.55–4.70 | w–m |
| 23.52–22.09 | 3.78–4.02 | w–vs |
| 24.03–23.39 | 3.70–3.80 | w–vs |
| 30.81–29.76 | 2.90–3.00 | w–m |
| 31.94–30.81 | 2.80–2.90 | w–m |
| 45.30–43.04 | 2.00–2.10 | w–m |

TABLE C

UZM-6

| 2-θ | d(Å) | I/I$_o$ % |
|---|---|---|
| 6.31–5.89 | 14.00–15.00 | w–m |
| 7.96–7.58 | 11.10–11.65 | m–s |
| 10.40–10.01 | 8.50–8.83 | w–m |
| 12.11–11.59 | 7.30–7.63 | m |
| 16.10–15.53 | 5.50–5.70 | m–vs |
| 19.28–18.55 | 4.60–4.78 | w–m |
| 22.26–21.60 | 3.99–4.11 | m |
| 23.20–22.43 | 3.92–4.00 | m–vs |
| 24.16–23.33 | 3.83–3.96 | w–s |
| 30.48–29.55 | 3.68–3.81 | s–vs |
| 31.94–30.92 | 2.80–2.89 | m |
| 44.83–43.47 | 2.02–2.08 | w |

The zeolites of this invention are capable of separating mixtures of molecular species based on the molecular size (kinetic diameter) or on the degree of polarity of the molecular species. When the separation of molecular species is based on molecular size, separation is accomplished by the smaller molecular species entering the intracrystalline void space while excluding larger species. The kinetic diameters of various molecules such as oxygen, nitrogen, carbon dioxide, carbon monoxide are provided in D. W. Breck, *Zeolite Molecular Sieves*, John Wiley and Sons (1974) p. 636.

The crystalline microporous compositions of the present invention either as synthesized or after calcination can be used as catalysts or catalyst supports in hydrocarbon conversion processes. Hydrocarbon conversion processes are well known in the art and include cracking, hydrocracking, alkylation of both aromatics and isoparaffins, isomerization, polymerization, reforming, dewaxing, hydrogenation, dehydrogenation, transalkylation, dealkylation, hydration, dehydration, hydrotreating, hydrodenitrogenation, hydrodesulfurization, methanation and syngas shift process. Specific reaction conditions and the types of feeds which can be used in these processes are set forth in U.S. Pat. Nos. 4,310,440 and 4,440,871 which are incorporated by reference. Preferred hydrocarbon conversion processes are alkylation of aromatics and isomerization of xylenes.

Other reactions may be catalyzed by these crystalline microporous compositions, including base-catalyzed side chain alkylation of alkylaromatics, aldol-condensations, olefin double bond isomerization and isomerization of acetylenes, alcohol dehydrogenation, and olefin dimerization, oligomerization and conversion of alcohol to olefins. Suitably ion exchanged forms of these materials can catalyze the reduction of $NO_x$ to $N_2$ in automotive and industrial exhaust streams. Some of the reaction conditions and types of feeds that can be used in these processes are set forth in U.S. Pat. No. 5,015,796 and in H. Pines, *THE CHEMISTRY OF CATALYTIC HYDROCARBON CONVERSIONS*, Academic Press (1981) pp. 123–154 and references contained therein, which are incorporated by reference.

The X-ray patterns presented in the following examples (and tables above) were obtained using standard X-ray powder diffraction techniques. The radiation source was a high-intensity X-ray tube operated at 45 kV and 35 ma. The diffraction pattern from the copper K-alpha radiation was obtained by appropriate computer based techniques. Flat compressed powder samples were continuously scanned at 2° (2θ) per minute from 2° to 70°(2θ). Interplanar spacings (d) in Angstrom units were obtained from the position of the diffraction peaks expressed as 2θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art, the determination of the parameter 2θ is subject to both human and mechanical error, which in combination can impose an uncertainty of about ±0.4 on each reported value of 2θ and up to ±0.5 on reported values for nanocrystalline materials. This uncertainty is, of course, also manifested in the reported values of the d-spacings, which are calculated from the θ values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m and w which represent very strong, strong, medium, and weak, respectively. In terms of 100×I/I$_o$, the above designations are defined as w=0–15; m=15–60; s=60–80 and vs=80–100. In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

EXAMPLE 1

An aluminosilicate reaction mixture was prepared in the following manner.

Aluminum sec-butoxide (95+%), 58.75 g, was added to 836.34 g TEAOH (35%) with vigorous stirring. To this mixture, 294.73 g colloidal silica, (Ludox AS-40, 40% $SiO_2$) was added, followed by the addition of 10.18 g distilled water. The reaction mixture was homogenized for 1 hr with a high-speed mechanical stirrer, and then aged in teflon bottles overnight at 95° C. After the aging step, the reaction mixture was recombined and analyzed, the analysis indicated a silicon content of 4.67%.

A 500 g portion of this reaction mixture was treated with TMACl solution consisting of 11.77 g TMACl (97%) dissolved in 23.0 g distilled water while applying vigorous mixing. After a half-hour of homogenization the reaction mixture was distributed among 8 teflon-lined autoclaves. The autoclaves were all placed in ovens set at 150° C., where the reaction mixtures were digested for 4 days at autogenous pressures. The solid products were recovered by centrifugation, washed, and dried at 95° C.

The composition of the isolated products consisted of the mole ratios Si/Al=6.88, N/Al=0.83 and C/N=6.05. Scanning Electron Microscopy (SEM) showed the crystallites to consist of clustered platelets approximately 100–300 nm across. Characterization by powder X-ray diffraction (XRD) showed the lines in the pattern to be those for the material designated UZM-5. Table 1 below shows lines characteristic of the phase. A portion of the sample was calcined by ramping to 540° C. at 2° C./min in $N_2$, holding at 540° C. in $N_2$ for 1 hr followed by a 7 hr dwell in air, also at 540° C. The BET surface area was found to be 530 $m^2/g$, and the micropore volume was 0.2 cc/g.

TABLE 1

| 2-θ | d(Å) | I/I$_o$ % |
|---|---|---|
| 6.24 | 14.15 | m |
| 7.90 | 11.18 | m |
| 10.32 | 8.57 | w–m |
| 12.00 | 7.37 | m |
| 15.80 | 5.60 | m–s |
| 16.34 | 5.42 | m |
| 19.05 | 4.66 | w–m |
| 22.00 | 4.04 | m |
| 22.86 | 3.89 | m |
| 23.80 | 3.74 | vs |
| 27.40 | 3.25 | w |
| 30.14 | 2.96 | w |
| 30.90 | 2.89 | w |
| 31.60 | 2.83 | m |
| 33.20 | 2.70 | w |
| 34.56 | 2.59 | w |
| 36.64 | 2.45 | w |
| 44.32 | 2.04 | w |

EXAMPLE 2

An aluminosilicate reaction mixture was prepared in the following manner. Distilled water, 876.65 g was used to dilute 846.25 g TEAOH (35%) solution. Aluminum sec-butoxide (95+%), 49.54 g was added with vigorous stirring. This was followed by the addition of 427.57 g of TEOS (98%). The reaction mixture was heated to 85° C. overnight and then distilled to 95° C. for 2 hr to remove solvent. The reaction mixture was allowed to cool and was found to contain 3.34% Si by elemental analysis. A 300 g portion of this reaction mixture was placed in a teflon beaker and mixed vigorously. A solution containing 3.8 g TMACl (97%), 0.3 g LiCl, and 1.1 g $Sr(NO_3)_2$ dissolved in 25 g distilled water was prepared and added slowly to the aluminosilicate concoction with mixing. After the addition, the reaction mixture was homogenized for 2 hr and then split up among four teflon-lined autoclaves. The autoclaves were placed in a 150° C. oven, where the reaction mixtures were digested for 5 days at 150° C. at autogenous pressures. The products were recombined, the solids isolated by centrifugation, washed, and dried at 95° C.

Analysis by powder x-ray diffraction showed the product to have the UZM-5 structure. A portion of the product was calcined under a flow of nitrogen for 7 hr at 580° C. The composition of the calcined product exhibited the following mole ratios as determined by elemental analysis: Si/Al=7.6, Sr/Al=0.11, Li/Al=0.06. The BET surface area of the calcined material was 500 $m^2/g$ and the micropore volume was 0.19 cc/g. The SEM of the product showed the crystals to consist of a rosette morphology, the plate bundles usually on the order of 0.3 to 0.8μ across. Characteristic lines in the x-ray diffraction pattern are shown below in Table 2.

TABLE 2

| 2-θ | d(Å) | I/I$_o$ % |
|---|---|---|
| 6.12 | 14.43 | m |
| 7.84 | 11.27 | m |
| 10.18 | 8.68 | w–m |
| 11.90 | 7.43 | m |
| 15.78 | 5.61 | m–s |
| 19.04 | 4.66 | w–m |
| 20.38 | 4.35 | w |
| 21.90 | 4.05 | m |
| 22.80 | 3.90 | m |
| 23.70 | 3.75 | vs |
| 25.22 | 3.53 | w |
| 26.26 | 3.39 | w |
| 30.06 | 2.97 | w |
| 31.40 | 2.85 | w–m |
| 33.18 | 2.70 | w |
| 44.13 | 2.05 | w |

EXAMPLE 3

An aluminosilicate reaction mixture was prepared by adding 17.22 g of Al(Osec-Bu)$_3$ (95+%) to 470.69 g TEAOH (35%) with vigorous stirring. De-ionized water was added, 8.41 g, followed by the addition of 103.67 g of Ludox AS-40 colloidal silica. The reaction mixture was homogenized for an hour with a high-speed stirrer before it was placed in a teflon bottle and aged at 95° C. for 2 days. After it was cooled it was determined by elemental analysis that the reaction mixture contained 3.46% Si. A 50 g portion of this reaction mixture was treated with a solution of TMACl (97%), 0.71 g, dissolved in 10 g de-ionized water. The mixture was homogenized for 30 minutes with a high-speed stirrer and then split among 3 teflon-lined autoclaves and digested for 2, 4, and 6 days at 150° C. at autogenous pressures. The solid products were isolated by centrifugation, washed with distilled water, and dried at 95° C.

The products of the reaction mixtures digested for 4 and 6 days were shown to be UZM-5 by powder x-ray diffraction. Characteristic lines in the x-ray diffraction pattern for the material observed after 6 days are given in Table 3.

TABLE 3

| 2-θ | d(Å) | I/I₀ % |
|---|---|---|
| 5.90 | 14.97 | m |
| 7.66 | 11.53 | m |
| 10.06 | 8.78 | w–m |
| 11.70 | 7.56 | m |
| 15.70 | 5.64 | m–s |
| 16.36 | 5.41 | w–m |
| 18.74 | 4.73 | w–m |
| 20.36 | 4.36 | w |
| 21.84 | 4.07 | m |
| 22.72 | 3.91 | w–m |
| 23.56 | 3.77 | vs |
| 26.20 | 3.40 | w |
| 27.26 | 3.27 | w |
| 29.94 | 2.98 | w |
| 31.26 | 2.86 | w–m |
| 33.08 | 2.71 | w |
| 43.92 | 2.06 | w |

EXAMPLE 4

This example shows the substitution of gallium for some of the aluminum in the structure. Two separate reaction mixtures, Mixture A, an aluminosilicate composition, and Mixture B, a gallosilicate composition, were prepared. Mixture A was prepared by adding 116.06 g Al(OsecBu)$_3$ (95+%) to 1982.41 g TEAOH (35%) with vigorous stirring. De-ionized water, 2.92 g, was added to the stirring reaction mixture along with 698.62 g Ludox AS-40 colloidal silica. The resulting mixture was homogenized for an hour with a high-speed stirrer before it was placed in teflon bottles and aged at 95° C. for one day. This aluminosilicate composition, Mixture A, contained 4.96% Si by analysis and a Si/Al ratio of 9.53. Mixture B was prepared by diluting 275.23 g TEAOH (35%) with 275.23 g de-ionized water. To this vigorously stirring solution, 107.77 g Ludox AS-40 colloidal silica and 36.2 g freshly precipitated Ga(OH)$_3$·xH$_2$O, 13.8% Ga, were added. After an hour of homogenization, the reaction mixture was placed in a teflon bottle and aged at 95° C. for three days. This gallosilicate composition, Mixture B, contained 3.21% Si by analysis.

The substituted aluminosilicate was prepared by combining 45 g Mixture A with 5 g Mixture B in a teflon beaker while employing high-speed stirring. A solution prepared by dissolving 1.17 g TMACl (97%) in 10.0 g de-ionized water was added to the stirring mixture. After a half-hour of homogenization, the reaction mixture was distributed among three autoclaves and digested for 4, 6, and 8 days at 150° C. at autogenous pressures. The solid products were isolated by centrifugation, washed with de-ionized water, and dried at 95° C.

All three of the products were shown to have the UZM-5 structure by powder x-ray diffraction. Elemental analysis showed the six day sample to consist of the following mole ratios: Si/(Al+Ga)=7.35; N/(Al+Ga)=1.11; Si/Ga=78.3; Al/Ga=15.0 and C/N=5.44. Characteristic lines in the x-ray diffraction pattern are given in table 4.

TABLE 4

| 2-θ | d(Å) | I/I₀ % |
|---|---|---|
| 6.06 | 14.57 | m |
| 7.80 | 11.33 | m |
| 10.16 | 8.70 | w–m |
| 11.84 | 7.46 | m |
| 15.72 | 5.63 | m–s |
| 19.04 | 4.66 | w–m |
| 20.38 | 4.35 | w |
| 21.822 | 4.07 | m |
| 22.76 | 3.90 | w–m |
| 23.66 | 3.76 | vs |
| 26.22 | 3.40 | w |
| 30.06 | 2.97 | w |
| 31.44 | 2.84 | w–m |
| 33.14 | 2.70 | w–m |
| 34.50 | 2.60 | w |
| 44.04 | 2.05 | w |

EXAMPLE 5

An aluminosilicate reaction mixture was prepared by adding 197.31 g Al(Osec-Bu)$_3$ to 2808.74 g TEAOH (35%), followed by the addition of 989.82 g colloidal silica (Ludox AS-40) while maintaining vigorous stirring. The reaction mixture was aged at 95° C. for 16 hr and then allowed to cool. This aluminosilicate reaction mixture was designated Mixture C and was used again in Example 7. Elemental analysis showed Mixture C to contain 4.79% Si. A portion of this reaction mixture, 110 g, was placed in a teflon beaker equipped with a high-speed stirrer. Separately, a solution was prepared by dissolving 1.27 g TMACl (97%) and 0.68 g NaCl in 6 g de-ionized water. This solution was added to the stirring aluminosilicate reaction mixture. After a half-hour of homogenization, the reaction mixture was divided among 4 teflon-lined autoclaves which were digested under a variety of conditions. The solid products were isolated by filtration, washed with de-ionized water, and dried at 95° C.

The products of all of the reactions exhibited the x-ray diffraction pattern of UZM-5. Characteristic lines in the x-ray diffraction pattern of a sample digested at 150° C. for 4 days are shown in table 5. Scanning Electron Microscopy showed the sample to be very uniform, consisting of rosettes of small plate-like crystals with the rosettes measuring from about 0.5 to about 2μ across. The BET surface area for this material was found to be 553 m$^2$/g, while the micropore volume was 0.22 cc/g. Elemental analysis showed the Si/Al ratio to be 5.97, Na/Al=0.19, N/Al=0.97, and C/N=5.59. Characteristic lines in the x-ray diffraction pattern for this material are given in table 5.

TABLE 5

| 2-θ | d(Å) | I/I₀ % |
|---|---|---|
| 6.16 | 14.33 | m |
| 7.76 | 11.39 | s |
| 10.12 | 8.73 | m |
| 11.82 | 7.48 | m |
| 15.74 | 5.63 | vs |
| 19.04 | 4.66 | m |
| 20.36 | 4.36 | w |
| 21.84 | 4.07 | m |
| 22.68 | 3.92 | s |
| 23.56 | 3.77 | vs |
| 26.18 | 3.40 | w |
| 27.02 | 3.30 | m |
| 29.98 | 2.98 | m |
| 31.32 | 2.85 | m |
| 33.12 | 2.70 | m |
| 44.10 | 2.05 | w |

EXAMPLE 6

An aluminosilicate reaction mixture was prepared using the following procedure: Aluminum sec-butoxide (95+%), 987.54 g, was added to 14058 g TEAOH (35%) with vigorous stirring. This was followed by the addition of 4954 g colloidal silica, Ludox AS-40. The reaction mixture was aged with stirring at 95° C. for 16 hr. After aging, the reaction mixture was found to contain 4.72% Si. This aluminosilicate reaction mixture was identified as Mixture D, and was used again in example 9. A portion of Mixture D, 47.01 g, was placed in a beaker equipped with a stirrer. Separately, a solution was prepared by dissolving 1.12 g TMACl (97%) in 1.87 g de-ionized water. While stirring the aluminosilicate reaction mixture, the TMACl solution was added, and the resulting mixture was further homogenized for 20 minutes. The reaction mixture was then placed in a 100 ml Parr stirred autoclave. The temperature of the reaction mixture was ramped from room temperature to 150° C. over a period of 3 hr, before it was held at 150° C. for 24 hr. The reaction mixture was digested at autogenous pressures. The solid reaction product was isolated by centrifugation, washed with de-ionized water, and dried at 100° C.

The product exhibited the diffraction pattern of UZM-5P. The characteristic x-ray diffraction lines for this material are shown in table 6 below. A reaction mixture of the same formulation, but digested for 72 hr instead of 24 hr, yielded well-crystallized UZM-5. The morphology of UZM-5P was plate-like with sub-micron dimensions as determined by Scanning Electron Microscopy. Elemental analysis showed the Si/Al ratio to be 6.0, N/Al=1.00 and C/N=6.07.

TABLE 6

| 2-θ | d(Å) | I/I$_o$ % |
|---|---|---|
| 6.16 | 14.33 | vs |
| 7.62 | 11.60 | m |
| 10.26 | 8.61 | s |
| 16.23 | 5.46 | m |
| 19.06 | 4.65 | m |
| 22.86 | 3.89 | vs |
| 30.38 | 2.94 | m |
| 44.22 | 2.05 | w |

EXAMPLE 7

A UZM-5P composition similar to that disclosed in example 6 was prepared in the following manner: 40 g of Mixture C (see Example 5), was used as the aluminum and silicon source and was placed in a beaker equipped with a high-speed stirrer. Separately, 0.92 g TMACl (97%) was dissolved in 40 g de-ionized water. This solution was added to Mixture C with vigorous stirring. After 20 minutes of agitation the reaction mixture was placed in a teflon-lined autoclave and digested at 150° C. for 4 days at autogenous pressures. The solid products were isolated by centrifugation, washed with de-ionized water, and dried at 95° C.

The product exhibited an x-ray diffraction pattern indicative of UZM-5P. Characteristic x-ray diffraction lines for this material are given in Table 7. Elemental analysis showed the material to have Si/Al=6.03, N/Al=1.07, and C/N=6.11. Scanning Electron Microscopy showed the sample to consist of clusters of bent plate-like crystals forming rosettes about 400–800 nm across.

TABLE 7

| 2-θ | d(Å) | I/I$_o$ % |
|---|---|---|
| 5.80 | 15.23 | s |
| 7.77 | 11.37 | m |
| 10.22 | 8.65 | m |
| 11.66 | 7.58 | m |
| 16.15 | 5.48 | m |
| 21.93 | 4.05 | w |
| 22.84 | 3.89 | m |
| 23.54 | 3.78 | vs |
| 30.00 | 2.98 | w |
| 33.02 | 2.71 | w |
| 44.04 | 2.05 | w |

EXAMPLE 8

An aluminosilicate reaction mixture was prepared in the following manner: TEAOH (35%), 846.25 g, was diluted with 876.65 g de-ionized water. Al(O-secBu)$_3$ (95+%), 49.54 g, was added to the hydroxide solution followed by the 15 addition of TEOS (98%), 427.57 g, while maintaining vigorous stirring. After two hours of homogenization, the reaction mixture was placed in a flask and aged at 75° C. with light stirring overnight. After the aging, the flask was fitted with a distillation head and some of the alcoholic hydrolysis products were removed via distillation. After solvent removal, the reaction mixture contained 3.34% Si. A 1200 g portion of this aluminosilicate reaction mixture was placed in a beaker equipped with a high-speed mixer. Separately, a solution was prepared by dissolving 15 g TMACl (97%) in 30 g de-ionized water. This solution was added dropwise to the aluminosilicate reaction mixture and further homogenized for a half-hour. The reaction mixture was then placed in a Parr 2-L static autoclave equipped with a teflon-cup liner. The reaction mixture was digested at 150° C. for 90 hr at autogenous pressures. The solid product was isolated by centrifugation, washed with de-ionized water, and dried at 95° C.

The product had an x-ray diffraction pattern consistent with that of the UZM-5P material, most notably the peaks at d=8.68 Å and 3.89 Å. Elemental analysis showed the Si/Al ratio=10.05, while the BET surface area was 601 m$^2$/g and the micropore volume 0.21 cc/g. Scanning Electron Microscopy showed the material to consist of uniform clusters of plate-like crystals in a rosette formation, with the rosettes having a diameter of about 0.25 to 0.5μ. Characteristic lines in the x-ray pattern for this material are given in Table 8 below.

TABLE 8

| 2-θ | d(Å) | I/I$_o$ % |
|---|---|---|
| 7.58 | 11.65 | m |
| 10.18 | 8.68 | m |
| 16.36 | 5.41 | m |
| 22.84 | 3.89 | m |
| 23.60 | 3.77 | vs |

EXAMPLE 9

A series of zeolites were prepared in a similar manner as the zeolite in example 6. In a beaker there were placed 47.01 g of mixture D (see Example 6) and to it there was added with stirring a solution of 1.12 g TMACl (97%) in 1.87 g of de-ionized water. The resulting mixture was homogenized for 20 minutes and then transferred to a 100 ml Parr stirred autoclave. Four other mixtures were prepared in a similar manner and the respective mixtures were heated to 150° C. and held at 150° C. for 12 hrs, 18 hrs, 24 hrs, 36 hrs, and 72 hrs under autogenous pressure. Each solid reaction product was isolated by centrifugation, washed with de-ionized water and then dried at 100° C.

The x-ray diffraction patterns of the five samples are presented in Table 9. The data show that additional diffraction lines are observed as the amount of digestion time is increased. It is clear that the peaks at d≈8.6 ø and d=3.9 Å (in bold) are common to all the synthesized materials, i.e. structures.

Without wishing to be bound by any particular theory, the following explanation is proposed. UZM-5 can be indexed on a tetragonal cell with a=12.4 Å and c=28.6 Å. Based on a tetragonal cells the 8.6 Å and 3.9 Å peaks have indices of 110 and 310 respectively. This suggest that ordering first occurs in the a and b directions and then in the c-direction. It appears that a large number of structures can be prepared by stopping the reaction at various times until about 36 hours where the UZM-5 structure is attained. By stopping the synthesis at various times, one can obtain zeolites with a range of different surface area, acidity and adsorption properties.

TABLE 9

| 12 hr UZM-5P | | 18 hr UZM-5P | | 24 hr UZM-5P | | 36 hr UZM-5 | | 72 hr UZM-5 | |
|---|---|---|---|---|---|---|---|---|---|
| d (Å) | I % | d (Å) | I % | d (Å) | I % | d (Å) | I % | d (Å) | I % |
|  |  | 16.00 | 100 | 14.33 | 100 | 14.92 | 47 | 14.29 | 37 |
|  |  |  |  | 11.27 | 19 | 11.38 | 28 | 11.33 | 33 |
| 8.57 | 38 | 8.68 | 32 | 8.61 | 62 | 8.73 | 25 | 8.72 | 24 |
|  |  |  |  |  |  | 7.43 | 22 | 7.44 | 33 |
|  |  | 5.40 | 9 | 5.53 | 39 | 5.62 | 60 | 5.66 | 61 |
|  |  |  |  |  |  |  |  | 5.51 | 42 |
|  |  |  |  | 4.65 | 17 | 4.66 | 17 | 4.68 | 22 |
|  |  |  |  |  |  |  |  | 4.48 | 2 |
|  |  |  |  |  |  | 4.33 | 2 | 4.35 | 5 |
|  |  |  |  |  |  | 4.06 | 5 | 4.06 | 51 |
|  |  |  |  |  |  |  |  | 3.96 | 49 |
| 3.88 | 100 | 3.88 | 50 | 3.89 | 88 | 3.90 | 14 | 3.90 | 25 |
|  |  |  |  | 3.75 | 54 | 3.76 | 100 | 3.76 | 100 |
|  |  |  |  |  |  |  |  | 3.55 | 6 |
|  |  |  |  |  |  | 3.39 | 6 | 3.40 | 6 |
|  |  |  |  |  |  | 3.28 | 8 | 3.29 | 12 |
|  |  | 2.93 | 12 | 2.95 | 16 | 2.98 | 10 | 2.97 | 11 |
|  |  |  |  | 2.84 | 8 | 2.85 | 15 | 2.85 | 17 |
|  |  |  |  |  |  | 2.70 | 13 | 2.71 | 13 |
|  |  |  |  |  |  |  |  | 2.60 | 7 |
|  |  | 2.06 | 5 | 2.05 | 14 | 2.05 | 8 | 2.05 | 6 |

EXAMPLE 10

An aluminosilicate reaction mixture was prepared in the following manner: Al(Osec-Bu)$_3$ (95+%), 116.09 g, was added to 1983.17 g TEAOH (35%) and 1.86 g de-ionized water with vigorous stirring. Then 698.88 g Ludox AS-40 was added, with continued stirring. After an hour of homogenization, the aluminosilicate reaction mixture was placed in several teflon bottles and aged at 95° C. for 3 days. After the aging process, elemental analysis showed the mixture to contain 5.01% Si and had a Si/Al ratio of 10.03. This reaction mixture is designated Mixture E. A portion of this aluminosilicate reaction mixture, 40.0 g, was placed in a beaker where it was stirred vigorously. Separately, 0.78 g TMACl (97%) was dissolved in 15.0 g de-ionized water. This solution was added to the stirring aluminosilicate reaction mixture in a dropwise fashion. The mixture was allowed to homogenize further for about an hour. The reaction mixture was then placed in a teflon-lined autoclave and digested at 150° C. for 6 days at autogenous pressures. The solid product was isolated by centrifugation, washed with de-ionized water, and dried at 95° C.

The product had an x-ray pattern consistent with UZM-6. Scanning Electron Microscopy (SEM) showed the material to consist of plate-like crystals about 0.1–0.4µ across and less than 0.05µ thick. The Si/Al ratio of the product UZM-6 was 8.34 by elemental analysis. The BET surface area of the sample was 520 m$^2$/g, with a micropore volume of 0.21 cc/g. Characteristic lines in the x-ray diffraction pattern are given in table 10.

TABLE 10

| 2-θ | d(Å) | I/I$_o$ % |
|---|---|---|
| 6.14 | 14.38 | m |
| 7.76 | 11.38 | m |
| 10.12 | 8.73 | m |
| 11.82 | 7.48 | m |
| 15.68 | 5.65 | s |
| 16.30 | 5.43 | m |
| 18.98 | 4.67 | m |
| 20.32 | 4.37 | w |
| 21.86 | 4.06 | m |
| 22.42 | 3.96 | s |
| 22.78 | 3.90 | m |
| 23.68 | 3.75 | vs |
| 25.24 | 3.53 | w |
| 26.28 | 3.39 | w |
| 26.88 | 3.31 | m |
| 27.34 | 3.26 | m |
| 29.64 | 3.01 | m |
| 30.08 | 2.97 | w |
| 31.44 | 2.84 | w |
| 33.20 | 2.70 | w |
| 44.14 | 2.05 | w |

EXAMPLE 11

An aluminosilicate reaction mixture was prepared in an identical manner to Mixture E described in example 10. However, the reaction mixture was determined to be slightly different by analysis, with a Si content of 4.79 wt % and a Si/Al ratio of 9.59. A portion of this aluminosilicate reaction mixture, 1100 g, was placed in a large beaker equipped with a high-speed stirrer. Separately, a solution was prepared by dissolving 4.14 g LiCl and 21.43 g TMACl (97%) in 65 g de-ionized water. This solution was added dropwise to the aluminosilicate reaction mixture with stirring and was homogenized for an hour. The reaction mixture was then transferred to a static 2-L Parr reactor and digested at 150° C. for 3 days at autogenous pressure. The solid product was isolated by filtration, washed with de-ionized water and dried at 95° C.

Powder x-ray diffraction on a sample of the product showed the pattern to be consistent with that for UZM-6. The Si/Al ratio was 7.58. The BET surface area was 512 m$^2$/g, while the micropore volume was found to be 0.18 cc/g. SEM of the calcined product showed it to consist of bent plate crystals, sometimes stacked, up to 0.1–0.4µ across and less that 0.05µ thick. Characteristic lines in the x-ray diffraction pattern are given in table 11.

TABLE 11

| 2-θ | d(Å) | I/I$_o$ % |
|---|---|---|
| 6.28 | 14.07 | m |
| 7.84 | 11.27 | s |

TABLE 11-continued

| 2-θ | d(Å) | I/I$_o$ % |
|---|---|---|
| 10.22 | 8.65 | m |
| 11.92 | 7.42 | m |
| 15.93 | 5.56 | m |
| 18.98 | 4.67 | m |
| 21.98 | 4.04 | w |
| 22.52 | 3.95 | vs |
| 22.92 | 3.88 | m |
| 23.76 | 3.74 | vs |
| 26.33 | 3.38 | w |
| 26.92 | 3.31 | m |
| 31.36 | 2.85 | m |
| 33.26 | 2.69 | m |
| 44.24 | 2.05 | w |

EXAMPLE 12

It is known that zeolites are capable of a variety of hydrocarbon conversion processes and find much of their utility in this regard. This example demonstrates the capability of UZM-5, UZM-5P, and UZM-6 to convert heptane to a variety of products. Calcined samples of these materials and for comparison, a steam-stabilized Y zeolite (SSY) were tested in a microreactor operating at atmospheric pressure. The UZM-5 from example 5 and the UZM-6 from example 11 were ammonium ion-exchanged after calcination to remove alkali and obtain the acid form. The feed was heptane, saturated at 0° C. in an H$_2$ carrier gas. The catalyst loading was 250 mg of 40–60 mesh particulates. The samples were pretreated at 550° C. for 60 minutes in H$_2$. The feed was introduced at a constant flow rate of 125 cc/min. The products were hydrogenated before going to the gas chromatograph. In this variable temperature program, the product stream was sampled at the following temperatures/times on stream: 25° C./0 hr, 450° C./0.33 hr, 500° C./1.10 hr and 1.45 hr, and 550° C./2.20 hr and 2.55 hr. The selectivities to the major products for each sample are given in Table 12 for the last data point collected at 550° C. The data show that UZM-5 and UZM-5P are comparable to SSY in ability to convert heptane, while UZM-6 is clearly much more active than SSY in heptane conversion. UZM-6 shows much more conversion to aromatic products than the other materials.

TABLE 12

| Sample | SSY | Ex. 1 UZM-5 | Ex. 5 UZM-5 | Ex. 8 UZM-5P | Ex. 11 UZM-6 |
|---|---|---|---|---|---|
| Temperature | 550° C. | 550° C. | 550° C. | 550° C. | 550° C. |
| Time on Stream (hr) | 2.55 | 2.55 | 2.55 | 2.55 | 2.55 |
| Methane | 0.58 | 1.35 | 1.67 | 0.44 | 3.27 |
| Ethane | 3.21 | 3.90 | 5.33 | 1.78 | 10.22 |
| Propane | 17.14 | 17.15 | 22.98 | 8.69 | 30.88 |
| Isobutane | 9.9 | 5.12 | 7.04 | 4.61 | 14.23 |
| n-Butane | 8.61 | 8.40 | 10.25 | 5.13 | 11.35 |
| Isopentane | 1.72 | 1.16 | 1.43 | 1.37 | 1.52 |
| n-Pentane | 1.18 | 1.24 | 1.45 | 0.65 | 1.26 |
| Benzene | 0.19 | 0.12 | 0.29 | 0.17 | 1.66 |
| Heptane | 55.58 | 60.73 | 48.31 | 75.98 | 19.9 |
| Toluene | 1.75 | 0.46 | 0.88 | 0.75 | 4.19 |

EXAMPLE 13

Another distinguishing feature of zeolites is the ability to adsorb molecules in their micropores. Such properties enable the utility of zeolites in adsorbent, separation, and selective catalytic applications. Adsorption measurements were performed using a standard McBain-Bakr. gravimetric adsorption apparatus. The samples were calcined at 560° C. to remove organic templates before they were loaded into the tubes. The samples were then activated at 350° C. overnight to remove adsorbed water from the pores. The samples were then exposed to a gas at several specific partial pressures and the amount of the gas adsorbed is expressed in terms of the weight percent of the sample. The data in the tables below demonstrate the ability of UZM-5 and UZM-5P to adsorb n-butane, isobutane, O$_2$, and SF$_6$

| P/P$_0$ (Partial pressure) | Ex. 1 UZM-5 | Ex. 5 UZM-5 | Ex. 8 UZM-5P |
|---|---|---|---|
| Adsorption of O$_2$ (T = −183° C.) | | | |
| | wt % O$_2$ | Wt % O$_2$ | wt % O$_2$ |
| 0.13 | 24.8 | 26.1 | 17.4 |
| 0.39 | 28.3 | 28.7 | 25.4 |
| 0.92 | 37.1 | 34.2 | 39.2 |
| Adsorption of n-butane T = 22° C. | | | |
| | wt % n-C$_4$H$_{10}$ | wt % n-C$_4$H$_{10}$ | wt % n-C$_4$H$_{10}$ |
| 0.04 | 7.9 | 9.4 | 4.6 |
| 0.12 | 9.6 | 11.0 | 7.1 |
| 0.30 | 11.7 | 12.7 | 11.4 |
| Adsorption of isobutane T = 22° C. | | | |
| | wt % i-C$_4$H$_{10}$ | wt % i-C$_4$H$_{10}$ | wt % i-C$_4$H$_{10}$ |
| 0.04 | 1.7 | 1.5 | 3.1 |
| 0.12 | 2.6 | 2.0 | 5.7 |
| 0.30 | 4.1 | 2.8 | 9.3 |
| Adsorption of SF$_6$ T = 22° C. | | | |
| | wt % SF$_6$ | wt % SF$_6$ | wt % SF$_6$ |
| 0.92 | 3.3 | 1.8 | 5.6 |

EXAMPLE 14

Another method for examining adsorption properties is to use TGA or Thermal Gravimetric Analysis. In such an apparatus, adsorption information at elevated temperatures is easy to acquire, as well as controlled delivery of the adsorption gasses. This is especially convenient for larger, less volatile adsorbates that are more easily studied and handled at higher temperatures. The tests were conducted on calcined samples. Approximately 50 mg of sample was placed in the TGA sample holder. The sample was then activated for 2 hr at 500° C. in a N$_2$ stream flowing at 127 cc/min. After the pretreatment, the sample was brought to 120° C. and an additional feed was cut in consisting of N$_2$ saturated with cis 1,2-dimethylcyclohexane at 25° C., which flows at 72 cc/min. Hence, the total flow rate past the sample was about 200 cc/min. The adsorption of the cis 1,2-dimethylcyclohexane was then monitored by TGA at 120° C. for an additional 250 minutes. The cis 1,2-dimethylcyclohexane adsorption after 5 and 250 minutes are given in terms of wt. % of the sample in table 14. The table shows that UZM-6 picks up the large cis 1,2-dimethylcyclohexane much more readily than UZM-5.

TABLE 14

| cis 1,2-dimethylcyclohexane (DMC) adsorption, T = 120° C. | | |
|---|---|---|
| | Ex. 1, UZM-5 wt. % cis 1,2-DMC | Ex. 10, UZM-6 wt. % cis 1,2-DMC |
| 5 minutes | 0.59 | 2.08 |
| 250 minutes | 1.18 | 2.59 |

We claim as our invention:

1. A microporous crystalline zeolite having a composition in the as synthesized form on an anhydrous basis in terms of mole ratios of the elements of:

$$M_m^{n+}R_r^{p+}Al_{(1-x)}E_xSi_yO_z$$

where M is at least one exchangeable cation selected from the group consisting of alkali and alkaline earth metals, "m" is the mole ratio of M to (Al+E) and varies from 0 to about 1.2, R is a nitrogen-containing organic cation selected from the group consisting of protonated amines, protonated diamines, protonated alkanolamines, quaternary ammonium ions, diquaternaryammonium ions, quaternized alkanolamines and mixtures thereof, "r" is the mole ratio of R to (Al+E) and has a value of about 0.25 to about 3.0, E is at least one element selected from the group consisting of Ga, Fe, Cr, In and B, "x" is the mole fraction of E and varies from 0 to about 0.5, "n" is the weighted average valence of M and has a value of about +1 to about +2, "p" is the weighted average valence of R and has a value of +1 to about +2, "Y" is the mole ratio of Si to (Al+E) and varies from about 5 to about 12 and "z" is the mole ratio of O to (Al+E) and has a value determined by the equation:

$$z=(m \cdot n+r \cdot p+3+4 \cdot y)/2$$

the zeolite characterized in that it has at least two x-ray diffraction peaks, one at a d-spacing of 3.9±0.12 Å and one at a d-spacing of 8.6±0.20 Å and has a tetragonal unit cell.

2. The zeolite of claim 1 characterized in that it has a x-ray powder diffraction pattern which contains at least the d-spacings and relative intensities of one of Tables A to C.

3. The zeolite of claim 1 where M is at least one metal selected from the group consisting of lithium, cesium, sodium, potassium, strontium, barium, calcium, magnesium and R is a quaternary ammonium cation.

4. The zeolite of claim 3 where the quaternary ammonium cation is selected from the group consisting of tetramethylammonium, tetraethylammonium, tetrapropylammonium, hexamethonium, diethyldimethylammonium, ethyltrimethylammonium and mixtures thereof.

5. The zeolite of claim 3 where M is sodium and the quaternary ammonium cation is a mixture of tetraethylammonium and tetramethylammonium.

6. The zeolite of claim 3 where M is lithium and the quaternary ammonium cation is a mixture of tetraethylammonium and tetramethylammonium.

7. The zeolite of claim 1 where M is a mixture of an alkali metal and an alkaline earth metal and R is a quaternary ammonium cation.

8. The zeolite of claim 7 where M is a mixture of lithium and strontium.

9. The zeolite of claim 7 where the quaternary ammonium cation is selected from the group consisting of tetramethylammonium, tetraethylammonium, hexamethonium, tetrapropylammonium, diethyidimethylammonium, ethyltrimethylammonium and mixtures thereof.

10. The zeolite of claim 9 where R is a mixture of tetramethylammonium and tetraethylammonium.

11. The zeolite of claim 1 where "m" equals zero and R is a quaternary ammonium cation selected from the group consisting of tetramethylammonium, tetraethylammonium, hexamethonium, tetrapropylammonium, diethyidimethylammonium, ethyltrimethylammonium and mixtures thereof.

12. The zeolite of claim 11 where the quaternary ammonium cation is a mixture of tetramethylammonium and tetraethylammonium.

13. A process for preparing a microporous crystalline zeolite having a composition in the as synthesized form on an anhydrous basis in terms of mole ratios of the elements of:

$$M_m^{n+}R_r^{p+}Al_{(1-x)}E_xSi_yO_z$$

where M is at least one exchangeable cation selected from the group consisting of alkali and alkaline earth metals, "m" is the mole ratio of M to (Al+E) and varies from 0 to about 1.2, R is a nitrogen-containing organic cation selected from the group consisting of protonated amines, protonated diamines, protonated alkanolamines, quaternary ammonium ions, diquaternaryammonium ions, quaternized alkanolamines and mixtures thereof, "r" is the mole ratio of R to (Al+E) and has a value of about 0.25 to about 3.0, E is at least one element selected from the group consisting of Ga, Fe, Cr, In and B, "x" is the mole fraction of E and varies from 0 to about 0.5, "n" is the weighted average valence of M and has a value of about +1 to about +2, "p" is the weighted average valence of R and has a value of +1 to about +2, "y" Is the mole ratio of Si to (Al+E) and varies from about 5 to about 12 and "z" is the mole ratio of O to (Al+E) and has a value determined by the equation:

$$z=(m \cdot n+r \cdot p+3+4 \cdot y)/2$$

the zeolite characterized in that it has at least two x-ray diffraction peaks, one at a d-spacing of 3.9±0.12 Å and one at a d-spacing of 8.6±0.20 Å and has a tetragonal unit cell; the process comprising forming a reaction mixture containing reactive sources of R, Al, Si and optionally E and/or M and reacting the reaction mixture at reaction conditions which include a temperature of about 100° C. to about 175° C. for a period of about 12 hr to about 2 weeks, the reaction mixture having a composition expressed in terms of mole ratios of the oxides of:

$$aM_{2/n}O:bR_{2/p}O:(1-c)Al_2O_3:cEO_3:dSiO_2:eH_2O$$

where "a" has a value of about 0 to about 2, "b" has a value of about 1.5 to about 30, "c" has a value of about 0 to about 0.5, "d" has a value of 5 to about 30, and "e" has a value of about 30 to about 6000.

14. The process of claim 13 where M is selected from the group consisting of lithium, cesium, sodium, potassium, strontium, barium, calcium, magnesium and R is a quaternary ammonium cation.

15. The process of claim 14 where the quaternary ammonium cation is selected from the group consisting of tetramethylammonium, tetraethylammonium, hexamethonium, tetrapropylammonium, dimethyldiethylammonium, ethyltrimethylammonium and mixtures thereof.

16. The process of claim 15 where the quaternary ammonium source is selected from the group consisting of hydroxide compounds, halide compounds, and mixtures thereof.

17. The process of claim 13 where the source of M is selected from the group consisting of halide salts, nitrate salts, acetate salts, hydroxides, sulfate salts and mixtures thereof.

18. The process of claim 13 where the source of E is selected from the group consisting of alkali borates, boric acid, precipitated gallium oxyhydroxide, gallium sulfate, ferric sulfate, ferric chloride, chromium chloride, chromium nitrate, indium chloride and indium nitrate.

19. The process of claim 13 where the aluminum source is selected from the group consisting of aluminum isopropoxide, aluminum sec-butoxide, precipitated alumina, Al(OH)$_3$, aluminum metal and aluminum salts.

20. The process of claim 13 where the silicon source is selected from the group consisting of tetraethyorthosilicate, fumed silica, colloidal silica and precipitated silica.

21. The process of claim 15 where the quaternary ammonium cation is a mixture of tetramethylammonium and tetraethylammonium.

22. The process of claim 14 where the quaternary ammonium cation is a mixture of tetraethylammonium and tetramethylammonium and "m" equals zero.

23. The process of claim 14 where the quaternary ammonium cation is a mixture of tetraethylammonium and tetramethylammonium and M is sodium.

24. The process of claim 14 when the quaternary ammonium cation is a mixture of tetraethylammonium and tetramethylammonium and M is lithium.

25. The process of claim 14 when the quaternary ammonium cation is a mixture of tetraethylammonium and tetramethylammonium and M is a mixture of lithium and strontium.

26. The process of claim 13 where the reaction conditions include a temperature of about 140° C. to about 160° C. for a period of about 2 days to about 5 days.

27. A hydrocarbon conversion process comprising contacting a hydrocarbon stream with a microporous crystalline zeolite at hydrocarbon conversion conditions to give a converted product, the microporous crystalline zeolite having a composition in the as synthesized form on an anhydrous basis in terms of mole ratios of the elements of:

$$M_m^{n+}R_r^{p+}Al_{(1-x)}E_xSi_yO_z$$

where M is at least one exchangeable cation selected from the group consisting of alkali and alkaline earth metals, "m" is the mole ratio of M to (Al+E) and varies from 0 to about 1.2, R is a nitrogen-containing organic cation selected from the group consisting of protonated amines, protonated diamines, protonated alkanolamines, quaternary ammonium ions, diquaternaryammonium ions, quaternized alkanolamines and mixtures thereof, "r" is the mole ratio of R to (Al+E) and has a value of about 0.25 to about 3.0, E is at least one element selected from the group consisting of Ga, Fe, Cr, In and B, "x" is the mole fraction of E and varies from 0 to about 0.5, "n" is the weighted average valence of M and has a value of about +1 to about +2, "p" is the weighted average valence of R and has a value of +1 to about +2, "y" is the mole ratio of Si to (Al+E) and varies from about 5 to about 12 and "z" is the mole ratio of O to (Al+E) and has a value determined by the equation:

$$z=(m \cdot n+r \cdot p+3+4 \cdot y)/2$$

the zeolite characterized in that it has at least two x-ray diffraction peaks, one at a d-spacing of 3.9±0.12 Å and one at a d-spacing of 8.6±0.20 Å and has a tetragonal unit cell.

28. The process of claim 27 where the hydrocarbon conversion process is selected from the group consisting of alkylation, isomerization, olefin dimerization and oligomerization and dewaxing.

* * * * *

UNITED STATES PATENT AND TRADEMARK OFFICE
CERTIFICATE OF CORRECTION

PATENT NO. : 6,613,302 B1  Page 1 of 1
DATED : September 2, 2003
INVENTOR(S) : Moscoso et al.

It is certified that error appears in the above-identified patent and that said Letters Patent is hereby corrected as shown below:

Column 17,
Line 31, replace "Y" with -- "y" --.

Signed and Sealed this

Second Day of December, 2003

JAMES E. ROGAN
*Director of the United States Patent and Trademark Office*